US010299438B2

(12) United States Patent
Öhrn et al.

(10) Patent No.: US 10,299,438 B2
(45) Date of Patent: May 28, 2019

(54) APPARATUS FOR FORMING AND WRAPPING MATERIAL

(75) Inventors: Lars Öhrn, Göteborg (SE); Mikael Liljegren, Romakloster (SE)

(73) Assignee: TRIOPLAST AB, Smalandsstenar (SE)

( * ) Notice: Subject to any disclaimer, the term of this patent is extended or adjusted under 35 U.S.C. 154(b) by 947 days.

(21) Appl. No.: 13/700,314

(22) PCT Filed: Jun. 23, 2011

(86) PCT No.: PCT/EP2011/060567
§ 371 (c)(1),
(2), (4) Date: Dec. 6, 2012

(87) PCT Pub. No.: WO2012/007259
PCT Pub. Date: Jan. 19, 2012

(65) Prior Publication Data
US 2013/0104503 A1    May 2, 2013

(30) Foreign Application Priority Data
Jul. 12, 2010  (EP) .................................. 10169230

(51) Int. Cl.
*A01F 15/08*     (2006.01)
*G01N 3/08*      (2006.01)
(Continued)

(52) U.S. Cl.
CPC ............ *A01F 15/071* (2013.01); *A01F 15/08* (2013.01); *A01F 15/10* (2013.01); *A01F 25/14* (2013.01);
(Continued)

(58) Field of Classification Search
CPC ....... B65B 11/008; B65B 11/58; B65B 57/02; B65B 57/10; A01F 15/0705;
(Continued)

(56) References Cited

U.S. PATENT DOCUMENTS 901,416 A * 10/1908 Best ...................... F22B 37/202
                                                      122/510
2,708,872 A *  5/1955 Lauck ................. A01F 15/0825
                                                      100/192
(Continued)

FOREIGN PATENT DOCUMENTS

WO    WO-92/05688 A1    4/1992
WO    WO-95/01716 A1    1/1995

OTHER PUBLICATIONS

International Search Report for PCT/EP2011/060567, dated Jan. 2, 2012; ISA/EP.

*Primary Examiner* — Stephen F. Gerrity
*Assistant Examiner* — Joshua G Kotis
(74) *Attorney, Agent, or Firm* — Harness, Dickey & Pierce, P.L.C.

(57) ABSTRACT

A forming and wrapping unit and method for forming material into a continuous bar and wrapping the material. The unit including a forming chamber for forming material into a continuous bar, a sheet wrapping device for wrapping the continuous bar, and a controller operating on the sheet wrapping device. The sheet wrapping device and the controller are adapted to be operable independently of a rate of feeding bulk material into the forming chamber. The method includes feeding material to a wrapping position while forming the material, wrapping a sheet around the material such that the sheet at least partly overlaps a previously wrapped portion of the sheet, and transferring the wrapped material from the wrapping position to a storage ready position. The feeding of the material to a wrapping position and wrapping a sheet around the material are separately operable.

15 Claims, 4 Drawing Sheets

(51) Int. Cl.
    *A01F 15/10*     (2006.01)
    *A01F 15/07*     (2006.01)
    *B65B 11/00*     (2006.01)
    *A01F 25/14*     (2006.01)
    *A01F 25/18*     (2006.01)

(52) U.S. Cl.
    CPC .......... *A01F 25/183* (2013.01); *B65B 11/008* (2013.01); *G01N 3/08* (2013.01); *A01F 2025/145* (2013.01)

(58) Field of Classification Search
    CPC .... A01F 15/04–15/06; A01F 15/071–15/0715; A01F 2015/072–2015/076; A01F 2015/0825; A01F 2025/142; A01F 2025/145; A01F 2025/183; A01F 25/183; A01F 2015/0866
    USPC ... 53/493, 47, 528–530, 176, 210, 439, 567, 53/399; 100/65, 66; 141/114, 71, 73
    See application file for complete search history.

(56) References Cited

U.S. PATENT DOCUMENTS

| | | | | |
|---|---|---|---|---|
| 3,513,464 A * | 5/1970 | Yarbro | A01F 15/148 | 100/99 |
| 3,687,061 A * | 8/1972 | Eggenmuller | A01F 25/14 | 100/145 |
| 3,854,396 A * | 12/1974 | Greytak | A01F 15/12 | 100/4 |
| 4,310,036 A * | 1/1982 | Rasmussen | A01F 25/14 | 100/112 |
| 4,653,553 A * | 3/1987 | Cox | A01F 25/14 | 100/191 |
| 4,685,270 A * | 8/1987 | Brambilla | A01F 15/071 | 53/176 |
| 4,712,354 A * | 12/1987 | Lancaster | B65B 11/008 | 53/176 |
| 4,866,909 A * | 9/1989 | Lancaster, III | B65B 11/008 | 53/399 |
| 4,951,452 A * | 8/1990 | Lundahl | A01F 15/046 | 100/98 A |
| 4,953,336 A * | 9/1990 | Lancaster, III | B65B 11/008 | 53/176 |
| 5,012,631 A * | 5/1991 | Hostetler | A01F 15/071 | 53/556 |
| 5,182,894 A * | 2/1993 | Bate | B65B 11/008 | 53/170 |
| 5,421,142 A | 6/1995 | Cullen | | |
| 5,433,058 A * | 7/1995 | Peterson | A01F 15/071 | 53/389.3 |
| 5,557,510 A * | 9/1996 | McIntyre | A01F 15/07 | 172/75 |
| 5,628,168 A | 5/1997 | Inman et al. | | |
| 5,661,956 A * | 9/1997 | Tardif | A01F 15/071 | 53/556 |
| 5,752,374 A * | 5/1998 | Allworden | A01F 15/04 | 100/100 |
| 5,950,410 A * | 9/1999 | O'Brien | A01F 15/042 | 100/88 |
| 6,202,389 B1 * | 3/2001 | Inman | A01F 25/14 | 141/313 |
| 6,430,897 B1 * | 8/2002 | Cameron | A01F 25/14 | 53/436 |
| 6,516,590 B2 * | 2/2003 | Inman | A01F 25/183 | 100/145 |
| 6,655,116 B2 * | 12/2003 | Cullen | A01F 25/14 | 53/527 |
| 6,708,478 B1 * | 3/2004 | Mesmer | A01F 15/0858 | 100/3 |
| 6,715,410 B2 * | 4/2004 | Boucher | A01F 15/145 | 100/191 |
| 6,776,198 B1 * | 8/2004 | Haines | B65B 1/12 | 141/10 |
| 8,065,859 B1 * | 11/2011 | Wingert | A01F 25/183 | 100/191 |
| 8,291,687 B2 * | 10/2012 | Herron | A01D 43/06 | 56/341 |
| 2002/0035816 A1 * | 3/2002 | Lacey | A01F 15/071 | 53/438 |
| 2004/0187468 A1 * | 9/2004 | Krone | A01F 15/0825 | 56/341 |
| 2007/0220839 A1 * | 9/2007 | Cullen | A01F 25/14 | 53/567 |
| 2008/0148703 A1 * | 6/2008 | Smith | A01F 15/0833 | 56/341 |
| 2009/0223179 A1 * | 9/2009 | Johnstone | A01F 15/071 | 53/562 |

\* cited by examiner

APPARATUS FOR FORMING AND WRAPPING MATERIAL

CROSS-REFERENCE TO RELATED APPLICATIONS

This application is a 371 U.S. National Stage of International Application No. PCT/EP2011/060567, filed on Jun. 23, 2011, which claims priority to European Patent Application No. EP 10169230.9, filed on Jul. 12, 2010. The contents of the above applications are incorporated herein by reference in their entirety

FIELD OF THE INVENTION

The present invention relates to a method for forming and wrapping material into a continuous bar, a forming and wrapping unit for forming material into a continuous bar and wrapping said material. The present invention relates also to an apparatus for forming material into a continuous bar and wrapping said material.

BACKGROUND OF THE INVENTION

Conventional baling of bulk products in general, and especially agricultural products such as grass, hay, silage or straw, comprises compressing the bulk material in the baling chamber of a baling apparatus to form a bale and subsequently wrapping the bale with a net or cover sheet, for example a protective film. By wrapping the bale with a protective wrapping, a controlled environment can be created within the bale. Such an environment may be aerobic or anaerobic. For instance, for the production of silage from grass, which requires anaerobic conditions, the protective film should provide a barrier against moisture, oxygen and UV light, and also provide mechanical protection of the bale. In other instances, such as wrapping of compostable waste, an aerobic environment may be desired.

Instead of round bales, large elongated bales have been popular for storing material such as fodder, hay, silage, etc. Such elongated bales are often formed using long tubes of plastic film, which are drawn over a preformed (compressed) bar of material. Alternatively, the material is pressed into the tubes. However, such tubes are inflexible and in practice limited to very few applications, since the dimensions of the tube are predetermined before starting the procedure of packing the material. Thus, if the material to be packaged is depleted before the plastic tube has been filled, the user has to cut off the tube before sealing the elongated bale. The left-over of the tube cannot be used for encapsulating another bar of material. This may result in large amounts of wasted plastic tubes and thus in unnecessary costs, since such plastic tubes are relatively expensive.

Also, the thickness of the plastic tube is predetermined. This is a disadvantage because depending on the intended application, such as production of silage, which requires high quality protection to achieve the anaerobic conditions, or simply weather protection, there are different requirements on the plastic tubes. For instance, production of silage requires a thicker plastic than weather protection. Furthermore, a more densely compressed material may require a thicker wrapping than loosely compressed or assembled bulk material. Due to the high price of polymeric materials, a plastic tube which is thicker than necessary for the application in question will result in unnecessary costs for the user and unnecessary use of plastic material, which is a disadvantage also from an environmental point of view.

Another problem with these tubes is that the form of the tube may affect the storage stability and the quality of the final product. If the base of the tube perpendicular its longitudinal extension is too narrow, the tube will collapse which causes formation of air pockets near the periphery of the bale resulting in the retention of moisture and oxygen in the bale, which is highly detrimental for silage production.

WO95/01716 discloses an apparatus for wrapping feed in plastic sheeting by progressively wrapping a sheet of plastic film around a bar of compressed feed, instead of threading a plastic tube around the feed. The apparatus comprises a movable frame, a feed receiving part in the frame as well as a plastic sheeting wrapping frame arranged to be rotatable around the feed to be wrapped. The apparatus further comprises a pressing screw or other means for compressing the feed into a continuous bar. The wrapping frame receives its driving force from a power transmission of a working machine, such as a tractor, via a revolving gearbox of the pressing screw. Thus, the revolving gearbox is coupled with a transmission of the working machine and to a transmission for revolving the plastic sheeting. Hence, the revolution of the plastic sheeting is dependent on the revolution of the pressing screw.

Even if the apparatus disclosed in WO95/01716 at least partly solves the problem of waste of plastic material due to left-over of tubes, there are several drawbacks with the apparatus described above. A problem is that the consumption of the plastic sheet is not controlled and cannot be influenced by a user of the apparatus. Furthermore, the rotation of the feed by the pressing screw makes the apparatus unsuitable for compressing large quantities of material comprising long straws, since the rotation of such material results in large friction forces at the periphery of the compression chamber. Another problem related to the rotation of the feed is that the apparatus is also unsuitable for handling material comprising very short straws, or particulate materials such as corn, since the rotation of these materials results in too low friction forces the periphery of the compression chamber, such that the material is not formed to a bar of sufficient density.

Therefore, there remains a need in the art for improved methods for wrapping bulk materials in general, and especially straw materials such as grass, hay or silage, as well as particulate materials, such that a controlled environment with desired properties within the wrapping is provided, and apparatuses used for this purpose.

SUMMARY OF THE INVENTION

It is the object of the present invention to at least partly alleviate the problems of the prior art and to provide an improved method for wrapping bulk material.

In one aspect, the invention achieves the above object by providing a forming and wrapping unit for forming material into a continuous bar and wrapping said material, which unit is adapted to be attached to a material providing unit for feeding said material to the forming an wrapping unit. The forming and wrapping unit comprises:

a forming chamber for forming material into a continuous bar, said chamber having an inlet opening for feeding material into the chamber and an outlet opening for discharging said continuous bar;

sheet wrapping means for wrapping said continuous bar; and control means operating on said sheet wrapping means, At least one of the sheet wrapping means and said control means is adapted to be operable independently of a rate of feeding material into the forming chamber. Preferably both said sheet wrapping means and said control means are adapted to be operable independently of the material feeding rate.

Since the material feeding and the wrapping are separately operable, the extent of overlap between adjacent layers or rounds of wrapping sheet can be chosen by the user such that a desirable number of layers or rounds of wrapping film can be provided at each portion of the continuous bar of material. Hence, the forming and wrapping unit may be used for wrapping many different kinds of materials and for different applications, which impose different requirements on the degree of protection provided by the wrapping. Consequently, the forming and wrapping unit may be used for silage making, weather protection or wrapping of compostable waste, and it may be used for two or more different applications without requiring any modification except suitably adjusting the operation of the sheet wrapping means in order to provide for each application the desirable degree of overlap between adjacent rounds of wrapping sheet. Thus, the forming and wrapping unit according to the invention offers convenient and cost-efficient wrapping of bulk material formed into a continuous bar.

The forming and wrapping unit may further comprise a guiding portion arranged as a continuation of said compression chamber, wherein said sheet wrapping means are arranged to wrap a sheet around the guiding portion. The guiding portion preferably comprises a plurality of longitudinally extending plates or bars which are mutually spaced apart so as to expose part of the material to be wrapped. Thus, good adherence of the wrapping sheet to the material is provided.

Further, the forming chamber may be adjustable in size and/or cross-section. Additionally or alternatively, the guiding portion may be adjustable in size and/or cross-section. Hence, the unit can be optimized for different applications, since the optimal size and cross-sectional shape of the forming chamber, and thus also of the resulting continuous bar of material typically varies for different materials. For example, for forming and wrapping grass, a large diameter of the forming chamber may be preferable, whereas for wrapping grain or corn a forming chamber having a larger base area may be preferable.

The adjustment may be made during operation of the unit (i.e. during feeding, forming and wrapping of the material).

Furthermore, the sheet wrapping means of the forming and wrapping unit may comprise at least one support arm having at least one sheet dispenser. The support arm may comprise a telescopic arm. Advantageously, a telescopic arm can be arranged to closely follow any shape of the forming chamber and bar of material formed. Using such a telescopic arm the sheet may be wrapped tightly around the (compressed) material, such that air pockets formed between the material and the sheet are avoided. In some applications, the presence of oxygen may negatively affect the storage stability of the wrapped material, and thus avoiding air pockets may result in improved storage stability and quality of the wrapped material. Further, such an arm is adapted to follow the form of the guiding portion even if the diameter or form of the guiding portion is adjusted. Thus, the bar may be relatively close to the ground during wrapping.

Alternatively, the sheet wrapping means of the forming and wrapping unit may be arranged on a guide rail.

The sheet wrapping means of the forming and wrapping unit according to the invention typically comprises between 1 and 6 sheet dispensers, and preferably between 2 and 6 sheet dispensers. A sheet dispenser is typically a roll of sheet arranged to be unwound. By using several rolls of sheet the number of interruptions for changing rolls can be reduced, and thus the forming and wrapping unit is more time-efficient. Furthermore, if the sheet of one or more rolls should break or run out, the user may increase the velocity of the remaining roll or rolls, such that a desirable number of layers or rounds of wrapping film can be provided at each portion of the continuous bar of material without stopping the operation to change the broken or depleted roll. The increase in velocity may be proportional to the number of broken or depleted rolls.

In embodiments of the invention, the forming and wrapping unit may further comprise at least one sensor device for monitoring a degree of compression of the material to be formed into a continuous bar. By receiving information about the density of the formed material, the user can suitably adapt either the feeding operation, if more or less densely compressed material is desired, or the user can suitably adjust the degree of overlap between adjacent rounds of wrapping sheet. Hence, optimized compression and wrapping can be achieved.

In some embodiments, the unit may comprise two or more sensor devices, preferably positioned at different locations within the forming chamber. Said at least one sensor device may be expandable.

The forming and wrapping unit according to the invention may be part of an apparatus for forming material into a continuous bar and wrapping said material, said apparatus comprising material providing means for feeding said material;
first control means operating on said material providing means; and
a forming and wrapping unit as described above, wherein said first control means operating on said material providing means and said control means operating on said sheet wrapping means are separately operable.

The material providing means for feeding said material may also be referred to as a feeder. The first control means operating on said material providing means (feeder) may also be referred to as a first regulator. The control means of the forming and wrapping unit operating on the sheet wrapping means (sheet wrapper) may also be referred to as a second regulator.

Thus, the invention also relates to an apparatus for forming material into a continuous bar and wrapping said material, comprising material providing means for feeding said material;
first control means operating on said material providing means;
sheet wrapping means; and
second control means operating on said sheet wrapping means, characterized in that said first control means and said second control means are separately operable.

In embodiments of the invention the apparatus comprises at least one wire attached at its proximal end to the material providing means or to a front wall of the forming and wrapping unit. The wire is typically released by a wire releaser during operation of the apparatus.

The apparatus may also comprise at least one device for measuring transfer of material formed into a continuous bar, wherein said device comprises:

at least one wire attached at its proximal end to the material providing means or to a front wall of the forming and wrapping unit;
a wire releaser adapted to release said wire; and means for measuring a release rate of said wire released by said wire releaser.

Such an arrangement is advantageous, since it is possible to measure the transfer of material formed into a continuous bar by said apparatus by measuring the release rate of the wire. Optionally, the speed of the wrapping means may be controlled based on the release rate of the wire, such that the overlap between adjacent rounds of sheet wrapped around the continuous bar may be controlled. Furthermore, a degree of compression of the material fed by the material providing means may be controllable using wire braking means which may be arranged in connection with the wire releaser.

Preferably the wire is arranged to be embedded in the material during feeding and wrapping of said material. Hence, in case the wire should break off during operation of the apparatus, it is dampened by the material and thus is less hazardous to the surroundings.

At its distal end, the wire may be attached to a corresponding wire supporting device located at a distal end of the bar of material. Preferably, the wire supporting device may be formed as a cone-shaped body and in use is at least partly wrapped within a sheet used for wrapping said continuous bar.

In a further aspect, the invention provides a method for forming and wrapping material into a continuous bar, comprising feeding said material to a wrapping position while forming said material;

wrapping sheet around said material such that said sheet at least partly overlaps a previously wrapped round of sheet;

transferring the wrapped material from said wrapping position to a storage ready position;

characterized in that said step of feeding the material to a wrapping position and said step of wrapping sheet around the material are separately operable.

The advantages of separate operation of the feeding and the wrapping have been described above.

By "storage ready position" is meant a position where the bar of material may be left and stored or from which it may be transferred to a more permanent storage location. A storage ready position may refer to the ground site on which the bar is intended to rest during storage, or from which it is to be transported to a subsequent storage site. A storage ready position may also refer to the platform of a vehicle. In such cases, the vehicle may be in motion, moving away from the apparatus or unit according to the invention. Alternatively, such a vehicle may be at rest. A storage ready position may also refer to a position on a conveyor belt, which may be running.

In some embodiments, the method further comprises monitoring a degree of compression of said material during feeding of said material. The method may also comprise measuring a release rate of a wire released during feeding of said material, wherein said step of wrapping sheet around said material is controlled based on the release rate of said wire.

Furthermore, the method according to the invention may further comprise at least one step of adjusting a diameter of a compression chamber used for forming of said continuous bar. Typically, the method may comprise one step of increasing a diameter of said continuous bar by increasing the diameter of the forming chamber of the forming and wrapping unit, and one subsequent step of decreasing said diameter of said continuous bar by decreasing the diameter of the forming chamber of the forming and wrapping unit.

In a further aspect, the invention provides a compression measuring device for measuring a degree of compression of bulk material, said measuring device comprising:

a sensor device at least partly embedded in said material and adapted to be subjected to a compressive force applied by the material on the sensor device; and a control device adapted for applying a predetermined actuation pulse to the sensor device in order to actuate said sensor device, wherein actuation of the sensor device produces a detectable response.

The sensor device may be employed in a method for measuring a degree of compression of a material, comprising the steps of providing an expandable sensor device at least partly embedded in said material and adapted to receive a compressive force applied by the material on the expandable sensor device, and applying a predetermined actuation pulse to a expandable sensor device in order to actuate said sensor;

detecting a response produced by said actuation pulse applied to the expandable sensor device.

Such a sensor device and method may be useful for monitoring the degree of compression of bulk material being formed by a forming chamber. In particular the device and the method may be useful for monitoring the degree of compression of material being formed into a continuous bar. Further, the method may be particularly useful in combination with a method for forming and wrapping material into a continuous bar as described herein. However, the sensor device may be useful also in applications where there is no wrapping operation, but only compression of material.

By monitoring the degree of compression of material, the operator of a packaging or forming apparatus may suitably adapt the operation (e.g. the feeding of material) in order to optimize the degree of compression. Hence, optimal compression of material can easily be achieved.

In embodiments of the invention, the sensor device may be expandable, for example having the form of an expandable bladder of a pair of tongs. Alternatively, instead of being expandable said sensor device may also be able to decrease in size as a result of said degree of compression.

In particular, the measuring device may be adapted to measure the degree of compression of material passing said measuring device. Typically, where the sensor device is expandable, said actuation pulse may expand the expandable sensor device in a direction perpendicular to a flow of material passing said sensor device.

The measuring device may further comprise means for measuring said response.

In a preferred embodiment, the expandable sensor device is formed as a pair of tongs and said actuation pulse is a force of a predetermined magnitude applied to expand the claws of said tongs, and the response to said pulse is the resulting distance between the claws.

In another preferred embodiment, the expandable sensor device is formed as an expandable bladder, which may be expanded by injecting a fluid through an inlet of the bladder, and said actuation pulse is a pressure of a predetermined magnitude by which fluid is injected into said bladder, and the response to said pulse is the volume expansion of said bladder.

The measuring device may be used in an apparatus for forming material into a continuous bar comprising material providing means and a compression chamber, wherein material provided by said material providing means is forced to pass through said compression chamber. Hence, the invention also relates to an apparatus for forming material into a continuous bar comprising:

material providing means;

a compression chamber, wherein material provided by said material providing means is forced to pass through said compression chamber; and a measuring device as described above arranged in said compression chamber.

The compression chamber may be a forming chamber as described herein.

These and other aspects of the present invention will now be described in more detail, with reference to the appended drawings showing embodiments of the invention. It is noted that the invention relates to all possible combinations of features recited in the claims.

DETAILED DESCRIPTION OF THE INVENTION

Figure 1:
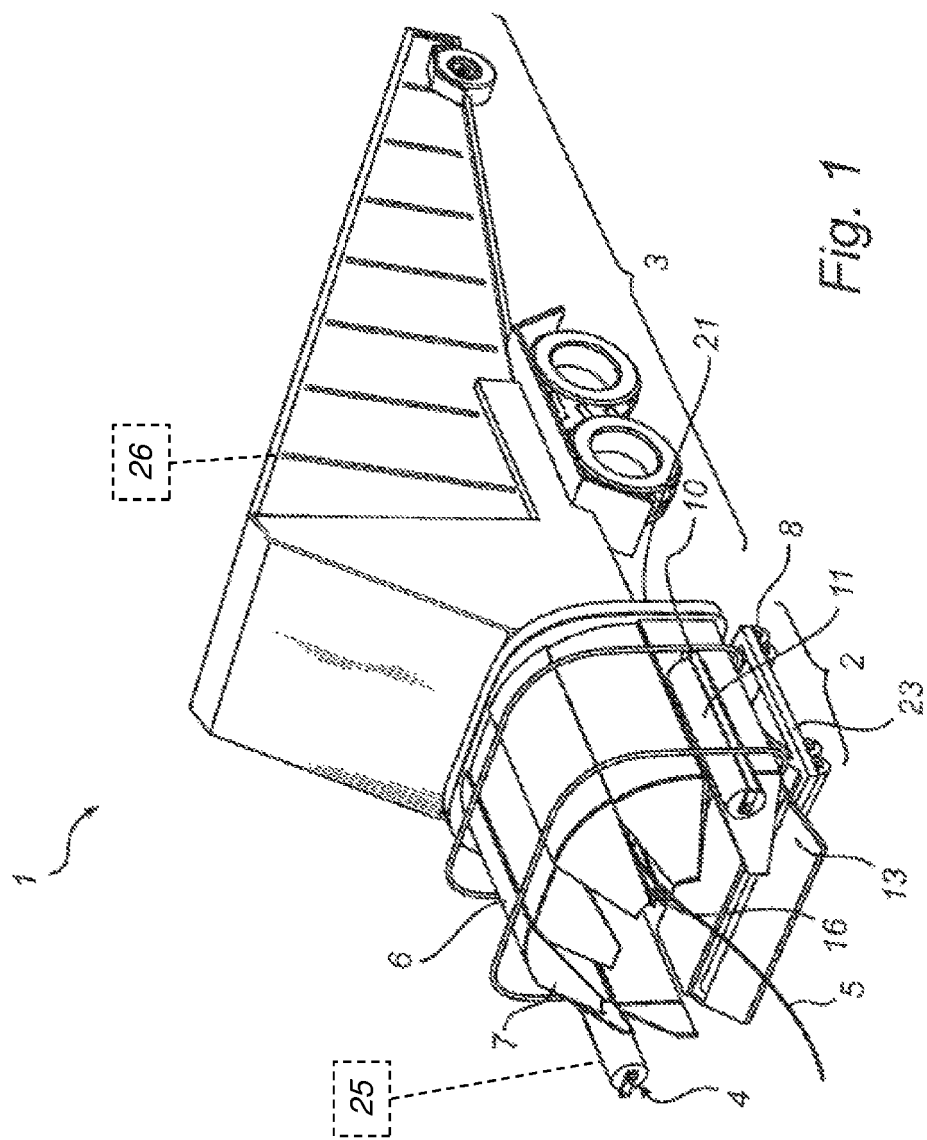
FIG. 1 is a schematic perspective view of an exemplary embodiment of an apparatus according to the invention.

FIG. 1 is a schematic view of an apparatus 1 for wrapping material into a continuous bar. The apparatus 1 in FIG. 1 may be divided into forming and wrapping unit in form of a compressing and wrapping part 2 and a feeder unit in form of a feeder part 3, which are connectable to each other. Even if the forming and wrapping unit is called compressing and wrapping part 2, the material is not necessarily compressed by the compressing and wrapping part 2. That is, in some applications little or no compression is suitable. In such a case the degree of compression of the material will be scarcely increased by the compressing and wrapping part 2. The compressing and wrapping part 2 of the apparatus 1 is connected to the feeder part 3 of the apparatus and comprises i.a. sheet wrapping means 4, a forming chamber in the form of a compression chamber 6 and a guiding portion 7 arranged as a continuation of said compression chamber 6. The feeder part 3 comprises suitable material providing means for feeding material to the compressing and wrapping part 2. Through the description words as above, below, upper and lower are intended to have their usual meaning, seen when the apparatus 1 is in use. Words distal and proximal are intended to have their ordinary meaning in relation to the apparatus 1. That is, distal is intended to mean further away from the apparatus 1 and proximal is intended to mean near the apparatus 1. The inlet side of the compressing and wrapping part 2 is defined as the side facing the feeder part 3 and the outlet side the opposite side, facing away from the feeder part 3.

The compression chamber 6 is adjustable in size and comprises an inlet at a front wall 21, an outlet on the opposite side of the front wall, an upper portion, and a base, which base is substantially horizontal in use. The upper portion comprises a plurality of slightly arched plates. The circumference of the upper portion is divided into segments by the plates, which plates overlap each other along the edges extending between openings, i.e. the inlet and the outlet, of the compression chamber 6. Such overlapping edges allow a size and a cross-section of the compression chamber 6 to be adjustable. When the size of the compression chamber is as large as possible the plates are disposed edge to edge. The plates of the compression chamber 6 are preferably made of metal, but may also be made of other materials such as plastic, polyester, or composite.

The base of the compression chamber 6 is supported by four cylinders 8, via a frame 23, which cylinders are rotatable in a direction of motion of the apparatus when the apparatus is in use. Two of the cylinders are 8 arranged at or near the outlet side of the compressing and wrapping part 2 and two of the cylinders 8 are arranged at or near the inlet side. The cylinders are attached to the frame 23 which extends between the cylinders and is provided such that a gap is formed between the two pairs of cylinders 8. The frame 23 is attached to and supports the compression chamber 6 near the front wall 21. Also, closer to the outlet side of the compression chamber, the frame 23 is arranged at a certain distance from the base of the compression chamber 6 to leave a space between the frame and the base and the compression chamber, such that roll of sheet may pass therebetween. The cylinders 8 extend along a transversal distance of the base of the chamber in relation to the direction of motion of the apparatus 1 when the apparatus 1 is in use. Such rotatable cylinders 8 facilitate transfer of the compressing and wrapping part 2 of the apparatus 1, since the cylinders 8 counteract the friction force of apparatus 1 against the ground. Alternatively, the base may be supported by one or several wheels in each corner of the base or some other suitable support elements that provide at least a similar function.

Figure 2:
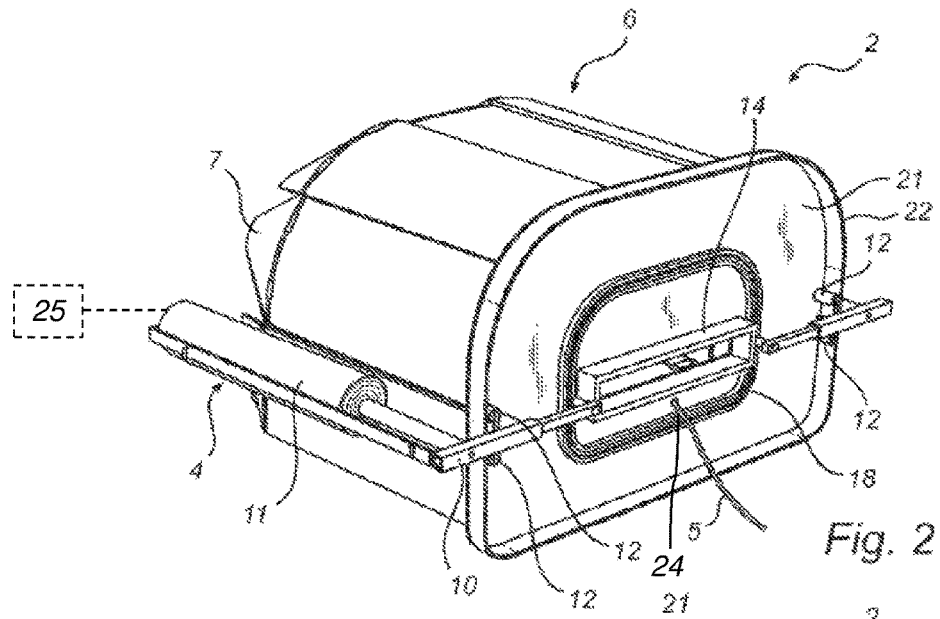
FIG. 2 is a schematic perspective view of a part of the exemplary embodiment in FIG. 1.
Figure 3:
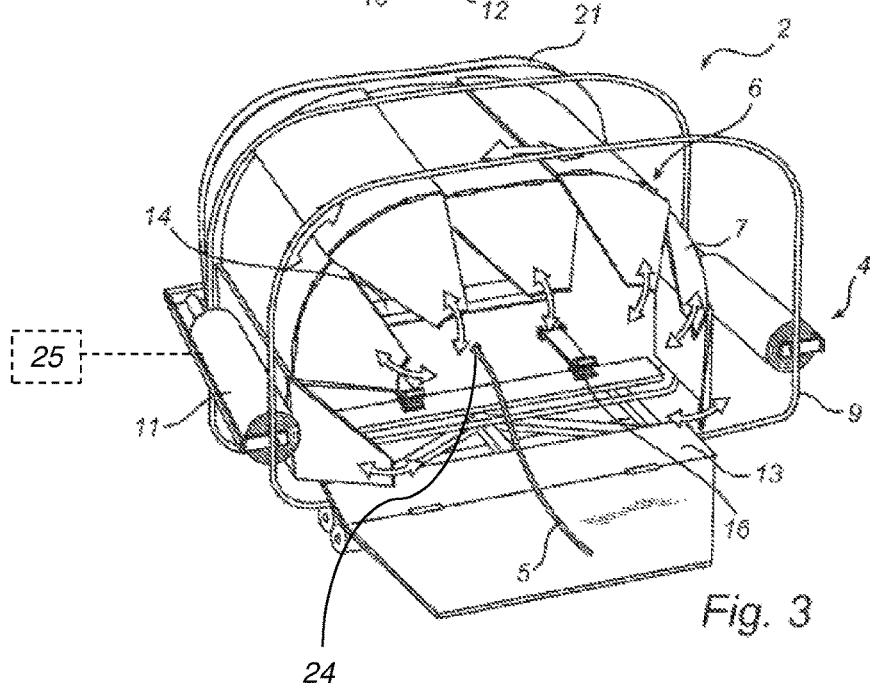
FIG. 3 shows another exemplary embodiment of a part of the apparatus.

It is noted that the compression chamber of FIGS. 1-3 does not have means for actively compressing the material to be formed into a bar. Rather, the compression chamber of these embodiments provides a confined space which receives material from a feeder, thus achieving compression of the material in the compression chamber.

The guiding portion 7 comprises a plurality of plates arranged as a continuation of the upper part of said compression chamber 6. The plates are hingedly attached to the plates of the compression chamber 6 and taper in direction from the compression chamber 6. In order to allow the cross-section of the compression chamber 6 to be adjusted and also to allow contact between a wrapping sheet and the material to be wrapped, the plates of the guiding portion 7 are arranged at a certain distance from each other. The plates may be angled in relation to the circumferential surface of the compression chamber 6, such that an end of the plate facing away from the compression chamber 6 is closer to a centre of the guiding portion 7 than an opposite end of the plate. By angling the plates of the guiding portion 7 towards the centre of the compression chamber 6, the diameter of the resulting continuous bar of material will be smaller. In addition, angling of plates of the guiding portion 7 results in a cone shaped end to the compression chamber 6. Hence, the degree of compression of the material formed to a continuous bar may be increased. The angling of the plates may be operated by wires (not shown) extending between each of the plates and a mechanism at the front wall 21 of the compression chamber, which mechanism may tighten the wire when increased angling is desired or release the wire when less angling is desired. Even if the guiding portion 7 is arranged as a continuation of the compression chamber 6 there may be a gap between the guiding portion 7 and the compression chamber 6. Since the cross-section of the compression chamber 6 is adjustable and since each plate of the guiding portion 7 is attached to a corresponding plate of the compression chamber 6, a size and a cross-section of said guiding portion 7 will be adjusted when the size or cross-section of the compression chamber 6 is adjusted. Thus, the resulting wrapped continuous bar may have different cross-sections and a user may choose a cross-section which is most convenient depending on for example the material to be wrapped or the intended storage space. For instance, a rectangular cross-section may be preferable if the user intends to transport the compressed bars using a tractor, since it is more space efficient to load such bars for instance on a platform of a vehicle.

The length of the compression chamber 6 and the guiding portion 7 together in an axial direction is preferably between 1 and 3 m, more preferably between 1 and 2.5 m and most preferably between 1.2 and 2.5 m. If the length is shorter than approximately 1 m, the material to be formed to a continuous bar will not be compressed as much as may be desired for many agricultural applications. For a too short compression chamber 6 and guiding portion 7 an expanding force of the compressed material will act on the wrapping material. Since the wrapping sheet does not counteract the expanding force as much as would be required to avoid any expansion, this results in unsatisfactory compression. To avoid this, the length of the compression chamber and guiding portion is preferably at least 1.2 m for many applications. On the other hand, if the length of the compression chamber 6 and the guiding portion 7 is longer than approximately 2.5-3 m, depending on the material, the feeder may not have any influence on the degree of compression of the material at the outlet side.

In embodiments of the invention, the length of the compression chamber 6 may be adjustable, such that a person operating the apparatus may choose an appropriate length for a specific application.

The sheet wrapping means (or sheet wrapper) 4 of the embodiment shown in FIG. 1 and FIG. 3 comprises two guide rails 9 and two sheet dispensers 11 for continuously applying a wrapping sheet around the material formed by the compression chamber 6. The guide rails 9 are arranged in parallel all the way around (encircling) the outer circumferential surface of the compression chamber 6 and the guiding portion 7. The sheet dispensers 11 are arranged using suitable fastening means between the guide rails 9 over the guiding portion 7 and partly over the compression chamber 6. The sheet dispensers 11 are arranged to follow the guide rails 9. Dimensions of the guide rails 9 may be fixed or may be adjustable to follow the shape of the compression chamber 6 and the guiding portion 7. Thus, the sheet dispensers 11 may be in close contact with the compression chamber 6 and the guiding portion 7 independently of the size or form of the compression chamber 6 and the guiding portion 7. Further, the dimensions of each of the guide rails 9 may be adjusted independently of each other. The sheet wrapping means 4 are operated by a hydraulic motor via a roller chain (not shown). Underneath the base of the compression chamber 6, the guide rails are arranged between the frame 23 and the base of the compression chamber 6 in the direction transversal to the material displacement, and between the cylinders 8 in the direction of material displacement. The sheet dispenser may thus pass in close proximity to the compression chamber end the material to be wrapped, not being hindered by either the frame 23 or the cylinders 8.

Furthermore, FIG. 1 shows also a lower support portion 13. Between the base of the compression chamber 6 and the lower support portion 13 there is a gap, such that the wrapping sheet may attach to the material that is formed to a continuous bar. The lower support portion 13 is formed as a plate, which is at one long side hingedly or fixedly connected to the frame 23 under the base of the compression chamber 6, such that the lower support portion 13 is supported by at least one of the cylinders 8 at the outlet side of the compressing and wrapping part 2. The opposite long side is free to rest on the ground. Thus, the continuous bar that is formed and wrapped using the apparatus 1 may be guided down to the ground via the support portion 13. Hence, damaging of the wrapping sheet may be prevented during feeding out of the wrapped continuous bar.

FIG. 2 shows an alternative embodiment in which the sheet wrapping means (sheet wrapper) 4 comprises a guide way 18, a support arm 10 in form of a telescopic arm, a sheet dispenser 11, a support roll 12, and second control means 25. The guide way 18 is arranged on a front wall 21 of the compressing and wrapping part 2 on the inlet side of the compression chamber 6 and follows substantially the shape of the front wall 21. The telescopic arm 10 has a maximum length that is adapted to extend from the guide way 18 to the outer circumferential surface of the compression chamber 6 when the compression chamber 6 has its largest circumferential extension. One end of the telescopic arm 10 is arranged to follow the guide way 18 and at an opposite end the sheet dispenser 11 is arranged. The sheet dispenser 11 is arranged over the guiding portion 7 and partly over the compression chamber 6, such that the free end of the sheet dispenser 11 protrudes beyond the guiding portion 7 on the outlet side. The sheet dispenser 11 is arranged to follow the circumferential (outer) surface of the compression chamber 6 when the telescopic arm 10 is moved along the guide way 18. On the side of the compressing and wrapping part 2 facing the ground, the sheet dispenser 11 may pass through the gap between the frame 23, the base of the compression chamber 6 and the cylinders 8.

The support roll 12 is arranged on the telescopic arm 10 at a distance from the end of the arm such that when the telescopic arm 10 is moved, the support roll 12 follows the inner surface of a perpendicularly protruding edge 22 of the front wall 21 of the compression chamber 6. The support roll 12 may extend between the telescopic arm 10 and the front wall 21.

A length of the telescopic arm 10 is controlled by the support roll 12. The telescopic arm 10 comprises a biasing means, which acts in a direction for extending the telescopic arm 10 to its full length. Since the support roll 12 abuts against the edge 22 of the front wall 21 and the sheet dispenser 11 is disposed on another side of the edge 22, the support roll 12 will hinder the biasing means from extending the telescopic arm 10 more than to the outer surface of the compression chamber 6. Alternatively, the length of the telescopic arm 10 may be controlled by an electrical sensor, which senses the edge of the compression chamber 6, in combination with a hydraulic cylinder, which controls the actual length of the telescopic arm 10 based on data from the electrical sensor.

In the embodiment in FIG. 2 each sheet wrapping means 4 comprises two support rolls 12, which are linked together. Thus, the support rolls 12 may more easily pass over overlapping portions of the plates of the compression chamber when the plates overlap each other. However, the number of support rolls 12 is not limited to two.

Alternatively, the guide way 18 may be arranged on or near the periphery of the compression chamber 6.

When using a sheet wrapping means comprising a support arm 10 instead of guide rails 9, the frame 23 and the cylinders 8 must be adapted so as to allow the sheet dispenser(s) to pass underneath the base of the compression chamber, preferably in close proximity of the chamber and the material to be wrapped. To this end, a smaller frame holding cylinders 8 may be provided below the lower support portion 13 only, close to the outlet side of the compression chamber (not shown in FIG. 2). The cylinders 8 of FIG. 1 located nearer to the inlet side of the forming and wrapping part may in this case be omitted. Optionally, support members or an additional support frame may be provided by which the compression chamber may be attached to the feeder part, and which may distribute part of the loading force of the compression chamber and the material contained therein to the feeder part. Such support members or additional support frame may also be connected to cylinders 8.

In embodiments of the invention, the sheet wrapping means 4 is operated by a hydraulic motor via a roller chain (not shown). However, the sheet wrapping means 4 may also be operated using other suitable power units, such as an electric motor or a hydrostatic motor. Alternatively, the roller chain may be replaced by a belt. The invention is not limited to any particular mechanical power transmission means; other suitable types of power transmission may also be used, such as electrical or hydrostatic.

In FIG. 1 the material providing means are integrated in the feeder part 3 of the apparatus 1 in form of a conventional rotor packer or feeder, which is arranged to feed the material to be compressed and wrapped through a rectangular opening using a rotor rotating around an axis transversal to the flow direction of the material. The feeder part 3 is connected to the compressing and wrapping part 2 of the apparatus 1 via the rectangular opening of the rotor packer/feeder, which opening is connected to a receiving end of a rectangular channel 14 provided in the front wall 21 of the compressing and wrapping part 2 on the inlet side thereof, see FIG. 2. The rectangular channel 14 provides a passage into the compression chamber 6 via an inlet opening and the walls of the channel 14 may be hingedly or fixedly arranged to the front wall 21 around the inlet opening. The feeder part 3 comprises also first control means 26 operating on said feeder and being separately operable in relation to the second control means 25 of the sheet wrapping means 4.

Alternatively, the material providing means may be a screw feeder. In such a case the channel may be modified for being compatible with such a feeder. Still alternatively, the material providing means may be a piston feeder. In such a case the channel may be modified to be compatible with such a feeder.

The compressing and wrapping part 2 may be operated by power from a separate power unit (not shown) arranged on the compressing and wrapping part 2, or by power from the feeder part 3, or by power from a tractor coupled to the compressing and wrapping part 2 or the apparatus 1. In all cases the control means 25 operating on said sheet wrapping means 4 are separately operable in relation to the first control means 26 operating on said feeder. The capacity of the compressing and wrapping part 2 is at least equal to the capacity of the feeder part 3.

The apparatus 1 further comprises a wire 5, which is arranged to be released by a wire releaser 24 disposed on the feeder part 3. The wire is intended to be embedded within the continuous bar of material during operation of the apparatus 1. The wire 5 runs through an opening disposed in the front wall 21 of the compression chamber 6. Alternatively, the wire releaser 24 may be arranged on a bottom side of the compression chamber 6 in the vicinity of the feeder. In use, a distal end of the wire 5 is attached to a corresponding wire 5 supporting device, which is a separate part from the compressing and wrapping part 2, arranged at a distal end of the bar that is formed by the apparatus 1 (not shown). Further, the wire releaser 24 comprises also means for measuring a release rate of the wire 5 (not shown). Such an arrangement is advantageous, since it is possible to measure transfer of material formed into a continuous bar by said apparatus 1 by measuring the release rate of the wire 5 that is released. Thus, the degree of rotation of the wrapping means 4 may be controlled based on the release rate of the wire 5. Consequently, overlap of the sheet layers wrapped around the continuous bar may be adjusted as required. Once enough material is formed into a continuous bar, the wire 5 is unlocked from the wire supporting device and drawn out from the continuous bar of material during winding the wire 5 at the wire releaser 24 using hydrostatic power (not shown). Since the wire 5 will be embedded within the continuous bar, the risk of injury is lowered in case of the wire 5 breaking off during drawing out. Alternatively, the wire 5 may be drawn out by first driving the apparatus 1 in a forward direction and thereafter in a backward direction. Thus, the wire 5 wound at the wire releaser 24 and drawn out from the continuous bar. In this case, the winding of the wire 5 works similarly to normal winding of a vacuum cleaner cord.

The wire releaser 24 may be provided with wire breaking means, which allows for controlling a degree of compression of the material provided by the material providing means. Depending on the application the suitable degree of compression may vary. For instance, when wrapping waste for composting a low degree of compression is suitable, since such applications require aerobic conditions within the wrapped continuous bar. In contrast, when wrapping material containing a high content of dry substance, a higher degree of compression is suitable, since it is desirable to decrease the air content in the bar. Further, when wet material (i.e. material containing a lower content of dry substance) is wrapped a slightly lower degree of compression compared to the case with dry material may be advantageous, since a low degree of compression may avoid or reduce problems with water being pressed out from the material during compression and wrapping as well as problems encountered when the material is taken out from the continuous bar after the desired process (e.g. storing) is finished.

Referring again to FIG. 3, this embodiment illustrates also how the size and form of the compression chamber 6 and the guiding portion 7 may be adjusted. When the size of the compression chamber 6 is decreased, the size of the guiding portion 7 is decreased as well. Since the plates of the compression chamber 6 are movably attached to the wall of the compression chamber, the plates are moved in relation to the front wall 21 when the size of the compression chamber and the guiding portion 7 is adjusted. Alternatively, the front wall 21 may be formed of several parts which overlap each other similarly to the plates of the compression chamber 6, when the size of the compression chamber 6 is adjusted, The size of the compression chamber of the embodiment in FIGS. 1 and 2 is adjusted similarly.

In embodiments of the invention, the apparatus 1 further comprises at least one sensor device 16 (see FIG. 3) which is a part of a compression measuring device for monitoring the degree of compression of the material provided by the material providing means. The sensor device 16 is disposed in the compression chamber 6 and adapted to receive/be subjected to a compressive force applied by the material. In the exemplary embodiment in FIG. 1 and FIG. 3 the sensor device 16 is formed as claws or a pair of tongs arranged on a rod which is attached to the front wall 21 of the compression chamber 6 that is facing the material providing means. The compression measuring device comprises also a control device, which is adapted for applying a predetermined actuation pulse to the sensor device 16 in order to actuate the sensor device 16.

The sensor device 16 provides data relating to the degree of compression of material. Based on data from the sensor device 16, a user may choose to adjust the material feed rate of the material providing means in order to obtain a desired degree of compression. Hence, the sensor device and the independently operable material providing means allow closely controlling the degree of compression of the material in the compression chamber 6.

In use, the sensor device 16 is at least partly embedded in the compressed material in the compression chamber 6 and the compression measuring device is adapted to measure the degree of compression of material passing said sensor device 16. The sensor device 16 is located in such a position within the compression chamber 6 where the material has already been compressed as much as possible. Alternatively, the sensor device 16 may be disposed at such a position that the data from the device may be interpreted using information relating to an expected maximal degree of compression.

The sensor device 16 is actuated by applying a predetermined actuation pulse in form of a predetermined force applied to expand the claws in a direction perpendicular to a flow of material passing the sensor device 16. Thereafter, the sensor device 16 produces a detectable response corresponding to a resulting distance between the claws. The response may be measured by the sensor itself or the measuring device may comprise means for measuring said response. For the embodiment in FIG. 1 the response may be measured using a sensor that measures the distance between the ends of the claws. Alternatively, if the force to the claws is applied by hydrostatic power the response may be measured as an amount of fluid that has been injected using a predetermined pressure. Hence, a specific degree of compression of the material results in a specific volume of fluid injected.

In an alternative embodiment, the sensor device 16 may be in form of an expandable bladder, which may be expanded by injecting a fluid through an inlet of the bladder. In such embodiment the actuation pulse is in form of a pressure of a predetermined magnitude by which fluid is injected into said bladder, and the response to said pulse is the volume expansion of said bladder. Before injection the fluid that is to be injected into the bladder is present in a reservoir, and the response may be measured by measuring a reduction of volume of the fluid in the reservoir. In this way, a volume of the fluid that is injected into said bladder may be determined.

In still an alternative embodiment, the sensor device is in form of a lengthwise expandable cylinder which is disposed axially within the compression chamber. The cylinder has an outer stationary cylinder and an inner movable cylinder. In such embodiment the actuation pulse is in form of a pressure of a predetermined magnitude by which the inner cylinder is imposed outwardly from the outer cylinder against the flow of the material. In other words, the sensor device of this embodiment is expanded in a direction against the flow of the material. If the pressure to the cylinder is applied by hydrostatic power the response may be measured as an amount of fluid that has been injected for applying the resulting force using a predetermined pressure. Alternatively, the cylinders may be filled with a fluid and the sensor device may be activated similarly to the embodiment using the bladder as described above. In such a case the response is a volume of fluid that can be injected into the cylinders. Still alternatively, the response may be detected as the distance by which the end of the inner cylinder is transferred.

The degree of compression may be measured by applying several actuation pulses with predetermined time intervals. After the actuation pulse is applied the resulting response is measured. Alternatively, the response may be measured continuously during the actuation pulse. A frequency of the time intervals is adjustable. The frequency is suitably chosen such that the sensor device is in its non-actuated state, that is a static state, between the pulses for a time period that is long enough for a certain amount of compressed material to pass the device. Thus an earlier pulse cannot affect the response to a subsequent pulse.

The sheet wrapping means 4 are operated by a hydraulic motor via a roller chain (not shown).

Figure 4A:
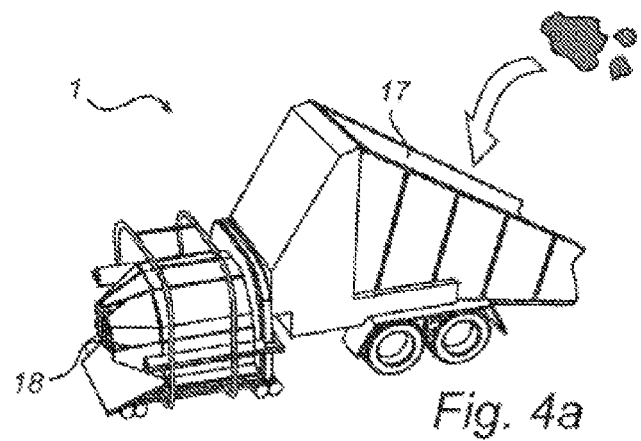
FIG. 4a-d is a series of figures illustrating the wrapping method.

FIG. 4*a*-*d* is a sequence of sketches illustrating use of an embodiment of the apparatus 1. FIG. 4*a* shows the apparatus 1 in the beginning of the wrapping procedure. The compression chamber 6 and the guiding portion 7 are adjusted such that they have the smallest possible cross-sections, and a wire supporting device in form of a cone-shaped body 18 is arranged at the guiding portion 7 on the outlet side of the compressing and wrapping part 2. The wire 5 is attached to the cone-shaped body 18 using a wire lock. Material that is to be formed to a continuous bar is loaded on a loading area 17 of the feeder part 3 of the apparatus 1 comprising the rotor feeder/packer. The material may be loaded by tipping material on a loader of a tractor on the loading area 17.

Figure 4B:
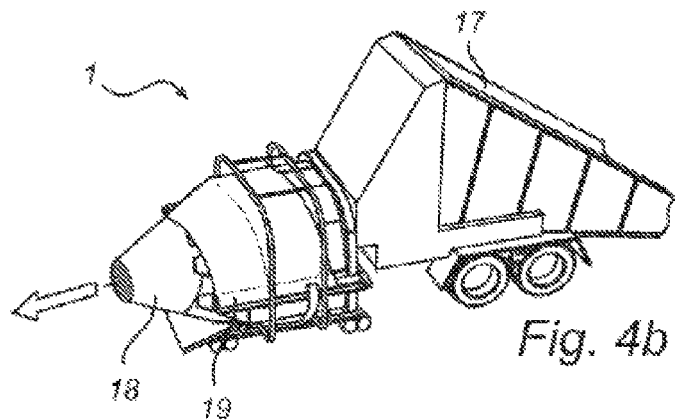

In FIG. 4*b* the cone-shaped body 18 is wrapped with a sheet 19 used for wrapping said continuous bar, and a beginning of a continuous bar is formed. The sheet is arranged on the sheet dispenser 11 (see FIG. 2 and FIG. 3), and the wrapping is accomplished by moving the sheet dispenser 11 in an "rotational" movement along the guide rails 9 in FIG. 1 and FIG. 3 or following the circumferential (outer) surface of the compression chamber using a telescopic arm which moves along the guide way 18 shown in FIG. 2. Preferably, the sheet 19 is self-adhering. By wrapping a self-adhering sheet such that one round of sheet is overlapping another round of sheet, the sheet will be secured around the cone-shaped body 18. Alternatively, the surface of the cone-shaped body 18 is provided with texture, such as grooves, circular recesses, protrusions or other suitable texture pattern. Thus, the sheet 19 may secured around the cone-shaped body 18 due to the frictional force between the sheet and the cone-shaped body 18. Still alternatively, the sheet 19 may secured to the cone-shaped body 18 by melting, using an adhesive or by tying the sheet 19. After the cone-shaped body 18 is wrapped with the sheet, the size and form of the compression chamber 6 and the guiding portion 7, respectively, is adjusted to a size that is suitable for the application. During the wrapping procedure, the feeder feeds material to the compression chamber 6, in which the material is compressed. At the outlet side of the compression chamber 6 the material is formed into a continuous bar 20. At the guiding portion 7 the sheet is wrapped around said material such that said sheet 19 at least partly overlaps a previously wrapped round of sheet 19. Since the sheet dispenser extend beyond the plates of the guiding portion 7 and there is a gap between the base of the compression chamber and the lower support element 13, the sheet 19 is wrapped partly over the plates and partly over and in contact with the material that is being formed into a bar 20. The operation of wrapping the sheet 19 around the material is separate from the operation of feeding the material to the compression chamber 6 and each operation is controllable independently of the other. Thereafter, the wrapped continuous bar of material is transferred to a storage ready position, which may be the ground or a temporary storage position such as a platform of a loader of a tractor. When the bar of material is transferred out from the apparatus 1, the sheet is drawn away from the compression chamber 6 and the guiding portion 7. During wrapping, a wire 5 is released downstream of the feeder and upstream of the compression chamber 6 such that the wire 5 is embedded within the continuous bar. Thus, by measuring the release rate of the wire 5 released during operation of the apparatus 1, transfer of material formed into a continuous bar by said apparatus 1 may be measured. The operation of wrapping sheet around the material is controlled based on the measured transfer of material. Since the control means 25 operating on the sheet wrapping means 4 and the first control means 26 operating on the feeder are separately operable, an operator of the apparatus 1 may easily adjust the resulting thickness of the wrapping covering the continuous bar by adjusting the speed of the sheet dispensers 11 thus influencing the degree of overlap between adjacent rounds of sheet 19. In the compression chamber 6 a degree of compression of the material is monitored during operation. Simultaneously, by controlling the feeder e.g. based on the compression data obtained from the measuring device, a desired degree of compression may be ensured.

During operation the operator may adjust the diameter of the compression chamber 6 and the guiding portion 7 if it for some reason is desirable. The optimum diameter and cross-section of the resulting continuous bar may vary depending on the properties of the material that is to be wrapped. For instance, for materials such as fodder, grass or the like a larger diameter is preferable. For instance for grain and such materials a larger base of the resulting continuous bar is preferable.

Figure 4C:
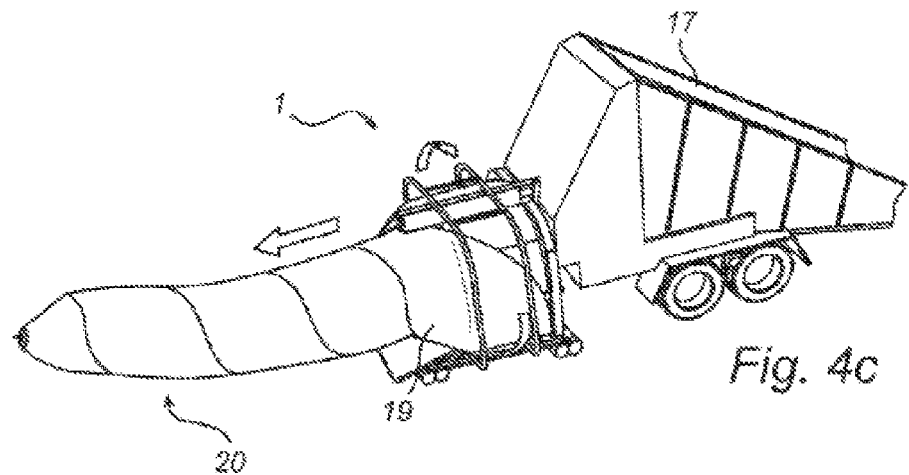

FIG. 4c illustrates the continuous bar 20 that is formed after some operation time. If the loading area of the feeder still comprises material, the feeder will continue to feed the material to the compression chamber 6 and the wrapping procedure will continue. The bar may get it longitudinal shape by moving either the apparatus 1 in a forward direction or by moving the wire supporting device in form of the cone-shaped body 18 in the direction opposite to the forward direction of the apparatus 1.

Figure 4D:
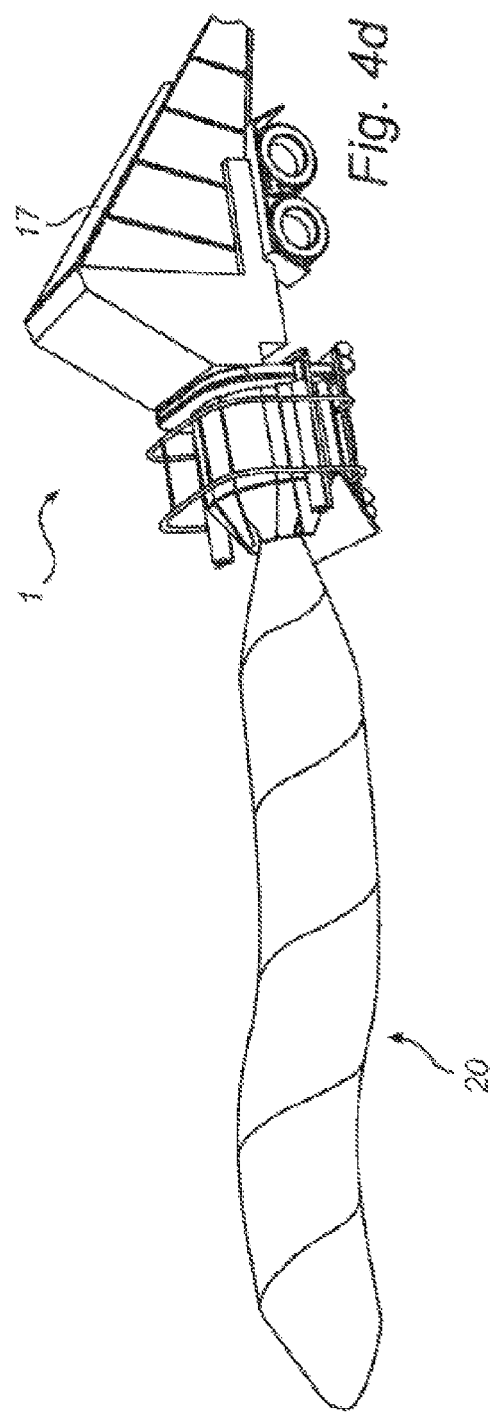

In FIG. 4d the bar 20 has gained the desired length and the diameter of the compression chamber 6 and the guiding portion 7 is decreased to the smallest possible for closing the end of the resulting continuous bar 20. Before sealing the continuous bar the wire 5 is released from the cone-shaped body 18 and drawn out from the bar by the apparatus 1. The wire is wound at the wire releaser 24 arranged under the feeder of the feeder part 3 using hydrostatic power of the feeder part 3. Since the wire 5 is embedded within the material the risk for injury is decreased if the wire 5 breaks off.

The sheet 19 used for wrapping may be a film, a net, or a mesh. Preferably, the sheet is a plastic stretch film, typically comprising polyethylene. Using a stretch film allows a higher wrapping force, which results in better adherence of the sheet 19. Thus, air pockets between the material that is formed to a continuous bar and the sheet 19 may be avoided. Further, a stretch film follows the shape of the continuous bar better than non-stretch film. Since the wrapping degree may be adjusted the stretch of the sheet may be adjusted, with the result that a stretch force of the sheet may be adjusted. Thus, consumption of sheet may be adjusted depending on the application and consequently the material that is to be wrapped. For compressing and wrapping crops intended for silage making, the wrapping film should protect the crop by providing a barrier against moisture and oxygen. The degree of protection provided by the wrapping may be determined by the properties of the sheet in combination with the number of layers wrapped around the compressed material. In order to improve protection of the compressed bar of material, a large degree of overlap may be used, such that the bar along almost its entire length is wrapped with at least two layers of sheet. However, for production of silage, at least part of the continuous bar is suitably covered with between 4 and 16 layers of sheet, and preferably with 6 layers of sheet. A plurality of layers can be accomplished by allowing the sheet dispenser to complete more than one turn around the continuous bar over the same area of the bar to produce overlapping or at least partially overlapping layers, and/or by having at least two sheet dispensers working simultaneously. Using a plurality of layers is advantageous since the controlled environment within the bar may be maintained even if one of the layers is damaged. In addition, the overlaps between the adjacent rounds of sheets will be tighter for a larger number of layers. Thus, the controlled environment within the bar is maintained better. Alternatively, for applications where less protection is required, the degree of overlap may be adjusted such that the continuous bar at any position along its entire length is covered with at least one layer of sheet, and at parts are covered with at least two layers. For instance, when material is wrapped in order to provide weather protection, less than 50% of the continuous bar may be covered with two layers of sheet.

Within the scope of the invention several modifications of the embodiments are possible. For instance, the number of sheet dispensers 11 may be preferably varied between one and six. However, a larger number of sheet dispensers 11 may also be preferable for some applications.

The feeder part 3 comprising the material providing means may be integrated in the apparatus 1 as is described above. Alternatively, the compressing and wrapping part 2 of the apparatus 1 may be an independent apparatus which is attached to a conventional feeder/packer comprising the material providing means. Such a conventional feeder may be a screw feeder, a rotor packer/feeder, or a piston feeder.

Alternatively, the transfer of material formed into a continuous bar 20 may be measured by using a belt conveyor or back stop. If a back stop is used the movement of the back stop is measured in some conventional way. The transfer of the material is simply equal to the movement of the backstop. If a belt conveyor is used the movement of the belt will equal the transfer of the material.

Alternatively, the size of the compression chamber 6 nor the guiding portion 7 is not adjustable, or the size of the compression chamber 6 is not adjustable while the plates of the guiding portion 7 may still be inclined as is described earlier.

Alternatively, the compressing and wrapping part 2 may include merely a compression chamber 6 and the guiding portion 7 may be excluded from the apparatus 1 comprising the compressing and wrapping part 2 or both the the compressing and wrapping part 2 and the feeder part 2. In such a case the preferred length of the compression chamber 6 and the guiding portion 7 refers to the length of the compression chamber 6 solely.

Still alternatively, the compressing and wrapping part 2 may include merely a guiding portion 7 and the compression chamber 6 may be excluded from the apparatus 1 comprising the compressing and wrapping part 2 or both the compressing and wrapping part 2 and the feeder part 2. In such a case the plates of the guiding portion 7 are attached to guiding units on the front wall for allowing change of the size of the guiding portion 7. The preferred length of the compression chamber 6 and the guiding portion 7 refers to the length of the guiding portion 7 solely. The sheet dispensers 11 may be arranged solely over the guiding portion 7 or over both the guiding portion 7 and the compression chamber 6. If the guiding portion 7 is excluded from the apparatus 1 the sheet dispensers 11 may bay arranged only over thee compression chamber 6.

Still alternatively, the wire 5 may be arranged at the bottom of the resulting continuous bar 20 instead of being embedded within the material.

The invention may be used for wrapping material independently of the desired conditions of the controlled environment within the continuous bar or the properties of the material that is to be wrapped. For instance, the invention may be used for baling of agricultural products, for instance for production of silage or storage of grain. Alternatively, the invention may be used for wrapping waste material for composting. In such a case, a perforated hose for air supply may be arranged within the material that is formed into a continuous bar during the compressing and wrapping procedure. The invention may also be used for wrapping oil-damaged soil for protecting the surrounding environment.

The invention claimed is:

1. A forming and wrapping unit for forming material into a continuous bar and wrapping said material, and adapted to be attached to a material providing unit, comprising:
   a forming chamber for forming said material into said continuous bar, said forming chamber having an inlet opening for feeding said material into said forming chamber and an outlet opening for discharging said continuous bar;
   a sheet wrapper configured to wrap said continuous bar with a plastic wrapping material;
   at least one wire attached to a front wall of said forming and wrapping unit, said at least one wire arranged to be embedded into said continuous bar during wrapping of said continuous bar; and
   a second regulator configured to operate said sheet wrapper independently of a rate of feeding material into said forming chamber such that said sheet wrapper wraps a first part of said continuous bar with a first predetermined number of layers of wrapping material and a second part of said continuous bar with a second predetermined number of layers of wrapping material,
   wherein a speed of said sheet wrapper is based on a measured release rate of said at least one wire.

2. The forming and wrapping unit according to claim 1, further comprising a guiding portion arranged as a continuation of said forming chamber, wherein said sheet wrapper is configured to wrap a sheet around at least part of said guiding portion.

3. The forming and wrapping unit according to claim 2, wherein said guiding portion is adjustable in at least one of size and cross-section.

4. The forming and wrapping unit according to claim 1, wherein said forming chamber is adjustable in at least one of size and cross-section.

5. The forming and wrapping unit according to claim 1, wherein said sheet wrapper comprises at least one sheet dispenser arranged on at least one guide rail.

6. The forming and wrapping unit according to claim 5, wherein said sheet wrapper comprises between 2 and 6 sheet dispensers.

7. The forming and wrapping unit according to claim 1, wherein said sheet wrapper comprises at least one support arm having at least one sheet dispenser.

8. The forming and wrapping unit according to claim 7, wherein said at least one support arm is telescoping.

9. The forming and wrapping unit according to claim 1, further comprising at least one sensor device for monitoring a degree of compression of said material.

10. The forming and wrapping unit according to claim 1, wherein said first predetermined number of layers of wrapping material of said first part of continuous bar are different in number from said second predetermined number of layers of wrapping material of said second part of continuous bar.

11. An apparatus for forming material into a continuous bar and wrapping said material, comprising:
    a forming chamber configured to form said material into said continuous bar, said forming chamber having an inlet opening to feed said material into said forming chamber and an outlet opening to discharge said continuous bar;
    a feeder for feeding said material;
    a first regulator configured to operate said feeder;
    a sheet wrapper configured to wrap said continuous bar with a plastic wrapping material;
    a second regulator configured to operate said sheet wrapper independently of said feeder such that said sheet wrapper wraps a first part of said continuous bar with a first predetermined number of layers of wrapping material and a second part of said continuous bar with a second predetermined number of layers of wrapping material; and
    at least one wire attached to one of said feeder and a front wall of said forming and wrapping unit, said at least one wire arranged to be embedded into said continuous bar during wrapping of said continuous bar,
    wherein a speed of said sheet wrapper is based on a measured release rate of said at least one wire.

12. The apparatus according to claim 11, further comprising, a wire releaser configured to release said at least one wire.

13. The apparatus according to claim 12, wherein said wire releaser is configured to measure the release rate of said at least one wire.

14. The apparatus according to claim 12, wherein a distal end of said at least one wire is attached to a corresponding wire supporting device at a distal end of said continuous bar of material.

15. The apparatus according to claim 11, wherein said first predetermined number of layers of wrapping material of said first part of continuous bar are different in number from said second predetermined number of layers of wrapping material of said second part of continuous bar.

* * * * *